United States Patent
Wang et al.

(10) Patent No.: US 9,139,507 B2
(45) Date of Patent: Sep. 22, 2015

(54) PROCESS FOR THE PREPARATION OF ALKYL 3-DIFLUOROMETHYL-1-METHYL-1H-PYRAZOLE-4-CARBOXYLATE AND ITS ANALOGS

(71) Applicant: KingChem LLC., Allendale Park, NJ (US)

(72) Inventors: Zheqing Wang, Union City, CA (US); Angang Wang, Dalian (CN); Yongcan Wang, Dalian (CN); Zhenwei Li, Dalian (CN)

(73) Assignee: KINGCHEM LLC., Allendale Park, NJ (US)

( * ) Notice: Subject to any disclaimer, the term of this patent is extended or adjusted under 35 U.S.C. 154(b) by 0 days.

(21) Appl. No.: 14/239,976

(22) PCT Filed: Dec. 9, 2013

(86) PCT No.: PCT/CN2013/088883
§ 371 (c)(1),
(2) Date: Feb. 20, 2014

(87) PCT Pub. No.: WO2015/085464
PCT Pub. Date: Jun. 18, 2015

(65) Prior Publication Data
US 2015/0158808 A1    Jun. 11, 2015

(51) Int. Cl.
| C07D 231/00 | (2006.01) |
| C07C 67/54 | (2006.01) |
| C07C 67/343 | (2006.01) |
| C07C 67/313 | (2006.01) |
| C07D 231/14 | (2006.01) |

(52) U.S. Cl.
CPC ............. *C07C 67/54* (2013.01); *C07C 67/313* (2013.01); *C07C 67/343* (2013.01); *C07D 231/14* (2013.01)

(58) Field of Classification Search
CPC .. C07D 231/14; C07D 231/12; C07D 231/16; C07D 403/12; A01N 43/56
USPC ....................................... 548/374.1; 560/174
See application file for complete search history.

(56) References Cited

U.S. PATENT DOCUMENTS

| 4,647,689 A | 3/1987 | Micinski |
| 4,883,904 A | 11/1989 | Amiet et al. |
| 5,093,347 A | 3/1992 | Graneto et al. |
| 5,498,624 A | 3/1996 | McLoughlin et al. |
| 7,358,387 B2 | 4/2008 | Lantzsch et al. |
| 7,678,924 B2 | 3/2010 | Walter et al. |
| 7,863,460 B2 | 1/2011 | Aihara et al. |
| 7,939,673 B2 | 5/2011 | Pazenok et al. |
| 8,115,012 B2 | 2/2012 | Sukopp et al. |
| 8,207,354 B2 | 6/2012 | Maywald et al. |
| 8,258,335 B2 | 9/2012 | Pazenok et al. |
| 8,269,020 B2 | 9/2012 | Bowden et al. |
| 8,314,233 B2 | 11/2012 | Zierke et al. |
| 8,344,157 B2 | 1/2013 | Wolf et al. |
| 8,350,053 B2 | 1/2013 | Pazenok et al. |
| 8,884,028 B2 | 11/2014 | Zumpe et al. |
| 2006/0149091 A1 | 7/2006 | Gallenkamp et al. |
| 2008/0004465 A1 | 1/2008 | Walter et al. |
| 2008/0154045 A1 | 6/2008 | Aihara et al. |
| 2009/0221588 A1 | 9/2009 | Haas et al. |
| 2011/0009642 A1 | 1/2011 | Pazenok |
| 2011/0040096 A1 | 2/2011 | Zierke et al. |
| 2011/0172436 A1 | 7/2011 | Wolf et al. |
| 2012/0065407 A1 | 3/2012 | McDougald et al. |
| 2012/0302608 A1 | 11/2012 | Hughes et al. |
| 2013/0012722 A1 | 1/2013 | Zumpe et al. |
| 2013/0123510 A1 | 5/2013 | Braun et al. |
| 2013/0197239 A1 | 8/2013 | Pazenok et al. |
| 2013/0274481 A1 | 10/2013 | Wang et al. |
| 2014/0107347 A1 | 4/2014 | Okamoto et al. |

FOREIGN PATENT DOCUMENTS

| CN | 102702104 A | 10/2011 |
| CN | 102766096 A | 7/2012 |
| CN | 102731402 A | 10/2012 |
| JP | 2013006778 A | 1/2013 |
| JP | 2013006779 A | 1/2013 |
| JP | 2013006780 A | 1/2013 |
| JP | 2013006782 A | 1/2013 |
| WO | 2011113788 A1 | 9/2011 |

(Continued)

OTHER PUBLICATIONS

Zhang G., and C. Zheng "Synthesis of Ethyl 4,4,4-Trifluoroacetoacetate" College of Chemistry & Chemical Engineering, Jiangau Teachers University of Technology 2007, 12 (46), pp. 823-824.*

(Continued)

*Primary Examiner* — Nyeemah A Grazier
*Assistant Examiner* — Sagar Patel
(74) *Attorney, Agent, or Firm* — Cantor Colburn LLP

(57) ABSTRACT

The disclosure provides a process for the preparation of alkyl 3-difluoromethyl-1-methyl-1H-pyrazole-4-caboxylate and its analogs. The process includes a reaction workup method for Claisen condensation, wherein the enolate salt is acidified after removing remaining starting material and byproducts such as, ethanol and excessive ethyl acetate. The process also includes a method for completely drying alkyl difluoroacetoacetate and its analogs before use in the next step by reacting trialkyl orthoformate with the residual water. The process includes using $Na_2CO_3$ and/or $K_2CO_3$ to promote the ring-closure reaction to produce the alkyl 3-difluoromethyl-1-methyl-1H-pyrazole-4-carboxylate. The process also includes effectively removing the regioisomer, alkyl 3-difluoromethyl-2-methyl-1H-pyrazole-4-caboxylate formed as a byproduct of the ring closure by a precipitation in a mixed solvent system and thereby eliminating the need for recrystallization of the final product.

22 Claims, No Drawings

(56) References Cited

FOREIGN PATENT DOCUMENTS

WO    WO 2011113789 A1 *  9/2011
WO       2012025469 A1     3/2012

OTHER PUBLICATIONS

Written Opinion and Search Report of the International Searching Authority for International Patent Application No. PCT/CN2013/088883; International Filing Date: Dec. 9, 2013; Date of Mailing: Sep. 5, 2014; 13 Pages.

Zhang et al., "Synthesis of Ethyl 4,4,4-Trifluoroacetoacetate"; College of Chemistry & Chemical Engineering; Jiangau Teachers University of Technology; No. 12; vol. 46; (2007); 2 pages.

Henne et al., "The Alkaline Condensation of Fluorinated Esters with Esters and Ketones" J. Am. Chem. Soc. vol. 69, (1947), pp. 1819-1820.

McBee et al., "The Preparation and Reactions of Fluorine-Containing Acetoacetic Esters" J. Am. Chem. Soc. vol. 75, (1953) pp. 3152-3153.

0-Dichlorobenzene "Material Safety Data Sheet", Fisher Scientific; www.fishersci.com; Downloaded Jun. 17, 2015; 7 Pages.

* cited by examiner

PROCESS FOR THE PREPARATION OF ALKYL 3-DIFLUOROMETHYL-1-METHYL-1H-PYRAZOLE-4-CARBOXYLATE AND ITS ANALOGS

CROSS-REFERENCE TO RELATED APPLICATIONS

This Application is a U.S. National Stage Application of PCT/CN2013/088883 filed Dec. 9, 2013 which is incorporated by reference in its entirety.

BACKGROUND

3-Difluoromethyl-1-methyl-1H-pyrazole-4-carboxylic acid (Formula I) is widely used for production of fungicides such as Isopyrazam and Sedaxane.

Annual production of fungicides exceeds 30,000 metric tons. Any improvement in cost efficiency or waste reduction, even if small, has large economic and environmental benefits.

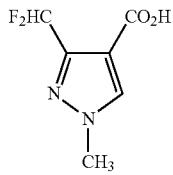

Formula I

A synthesis of Formula I was first published in U.S. Pat. No. 5,093,347 and consisted of four steps.

Alkyl difluoroacetate of Formula II reacts with alkyl acetate of Formula III via Claisen ester condensation to give the enolate salt of alkyl difluoroacetoacetate of Formula IV.

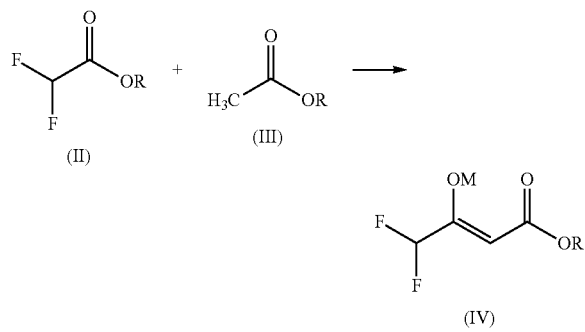

The enolate salt of Formula IV is then acidified to release the free alkyl difluoroacetoacetate of Formula V.

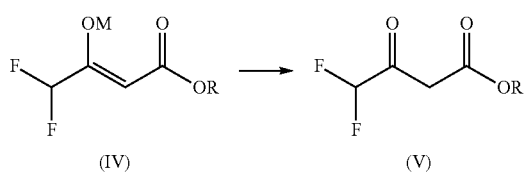

The alkyl difluoroacetoacetate of Formula V is coupled with trialkyl orthoformate in the presence of excess acetyl anhydride to provide the intermediate of Formula VI.

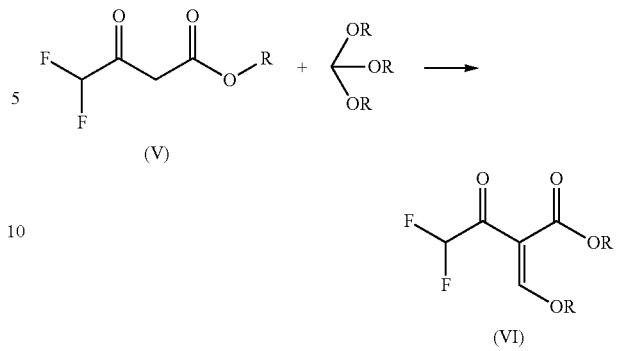

The intermediate of Formula VI is then reacted with methylhydrazine hydrate in the presence of NaOH/KOH to form the alkyl ester of 3-difluoromethyl-1-methyl-1H-pyrazole-4-carboxylic acid of Formula VII.

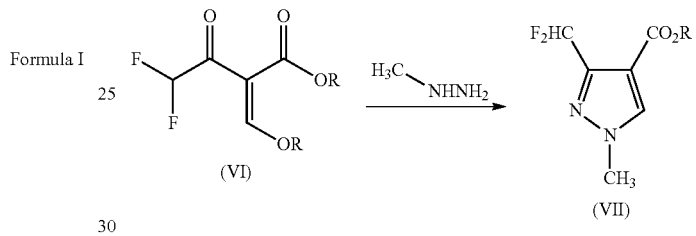

Basic hydrolysis of the alkyl ester of Formula VII, followed by acidification, results in the title product of Formula I.

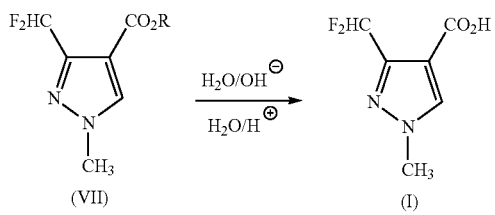

Many other patent and non-patent publications have reported synthetic methods for preparing alkyl 3-difluoromethyl-1-methyl-1H-pyrazole-4-carboxylate of Formula VII. But, most of the published synthetic routes are the same as the original route in principal. A great deal of effort has focused on improving the reaction conditions and/or work up methods.

For decades, the work up process of the Claisen condensation has been unchanged. After the Claisen condensation is finished, a protic acid in aqueous solution, such as HCl, HBr, $H_2SO_4$, $H_3PO_4$, or acetic acid, is added to neutralize the enolate salt of the ester. The organic phase is then separated from the aqueous phase, the aqueous phase is extracted with organic solvent 2-3 times, the combined organic phases are washed with water and/or brine, the organic solution is dried over a drying agent, then filtered and concentrated to remove the organic solvent and low boiling point impurities to obtain the crude alkyl difluoroacetoacetate. The crude alkyl difluoroacetoacetate is then purified by high vacuum distillation.

Separating the organic phase from the aqueous phase is difficult due to the presence of the highly soluble alkyl alcohol generated in the condensation. The alkyl alcohol interferes with the two phase separation process.

Residual water in the product, free alkyl difluoroacetoacetate of Formula V, is also detrimental to the next coupling reaction. To completely remove the residual water from the organic phase, high vacuum and high heat must be applied during fractional distillation. For an industrial scale reaction this step of the synthesis requires 20-30 hours. The whole process of extraction, drying, evaporation and fractional vacuum distillation for an industrial scale synthesis of 3-difluoromethyl-1-methyl-1H-pyrazole-4-carboxylic acid requires several working days to finish. Additionally, the huge amount of used and contaminated drying agents cannot be easily treated and disposed.

An additional shortfall of this procedure is the decomposition of the desired product (Formula V) during the distillation under high temperature. It is well known that hydrolysis followed by decarboxylation of the β-keto-esters occurs to yield a ketone, an alcohol, and carbon dioxide.

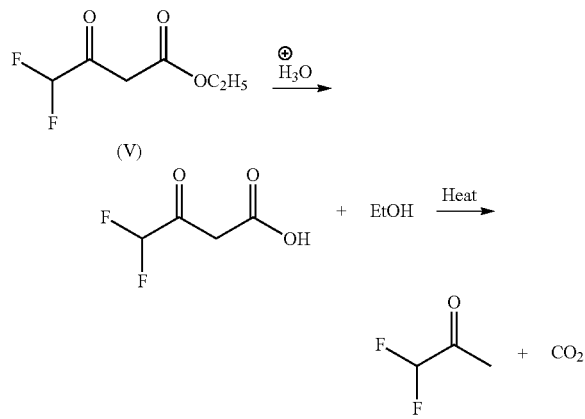

The inefficiencies in the alkyl difluoroacetoacetate (Formula V) synthesis can reduce product yield by 10-15%, reduce the facility's productivity, and generate huge amounts of drying agent waste.

WO 2009/106619 describes an improved work up method to avoid the difficulties in separation and distillation for the process described above. In the WO 2009/106619 method after the Claisen condensation is complete, an acid, such as concentrated $H_2SO_4$, formic acid, p-toluenesulfonic acid, or methanesulfonic acid, is added to the reaction mixture to acidify the basic enolate salt, and to release free alkyl difluoroacetoacetate. Alternatively, a gaseous acid, such as HCl gas or HBr gas is introduced into the reaction mixture accompanied by a small amount of water. The pressurized HCl or HBr gas is bubbled into the reaction mixture for several hours to release free alkyl difluoroacetoacetate. This procedure has the disadvantage of producing a precipitated solid, as NaCl, $Na_2SO_4$, sodium methylsulfonate, or sodium formate, which must be removed.

Though the WO 2009/106619 method provides an improvement in the Claisen condensation reaction workup, which increases yield, the method has obvious disadvantages. The removal of the resultant salts, such as NaCl, $Na_2SO_4$, sodium methylsulfonate, and sodium formate is time consuming. The filtered cake is washed four times with a large volume of ethyl acetate, increasing the chemical cost. Since excess HCl gas is introduced, the excess HCl gas must be removed, for example by vacuum pump. Due to the highly corrosive nature of HCl, extra costs must be incurred to protect the safety of manufacturing personnel and insure the continued functioning of the manufacturing facility. For example, all facility equipment must be fitted with corrosion resistant materials that meet corrosion resistance standards.

WO 2011/113789 provides a minor improvement over WO 2009/106619. In the WO 2011/113789 method after the Claisen condensation is complete, the pressurized HCl gas is introduced for several hours without the addition of water. The resulting sodium chloride is not removed. The whole reaction mixture including the product, impurities, and the inorganic solid in a mixture of ethyl acetate and ethanol, is then directly transferred into another reactor for the next step. The transfer of the mixture, which is very viscous, is difficult. Moreover, the disadvantages described for the WO 2009/106619 mentioned above are still present.

To date, all reported 3-difluoromethyl-1-methyl-1H-pyrazole-4-carboxylic acid synthesis methods proceed via a Claisen condensation, and require removing alkyl alcohols resulting from the reaction and excess alkyl acetate starting material by distillation after acidification. As discussed, this procedure has a number of disadvantages including waste generation, suboptimal yield, and long reaction workup time.

There are also considerable disadvantages to the drying methods reported for preparing fluoro acetoacetate for the subsequent coupling reaction. US 2012-0302608 uses a large amount of 4 Å molecular sieve powder to absorb the water. Other reported methods use Drierite (anhydrous calcium sulfate) to absorb residual water. Another approach employs a large volume of solvents such as ethyl acetate, cyclohexane, petroleum ether, or toluene for azeotropic distillation to drive the water out of the system. All these methods increase the chemical cost and are time consuming. None are particularly effective as 0.5-3.0% v/v residual water remains for each previously reported drying method.

U.S. Pat. No. 7,863,460 provides a method for selectively producing high purity ethyl 3-trifluoromethyl 1H-pyrazole-4-carboxylate in a two phase system in which the reaction is promoted by NaOH or KOH. After the reaction is complete the two phases are separated and the aqueous phase is extracted. The combined organic phases are dried over drying agent, and after filtration the filtrate is evaporated to give the crude ester as a white solid. The ester of Formula VII is finally hydrolyzed by NaOH/KOH aqueous solution, followed by acidification with HCl/$H_2O$ to produce the final product of Formula I. A disadvantage of this process is the simultaneous formation of the regioisomer of Formula X, which must be removed by additional crystallizations.

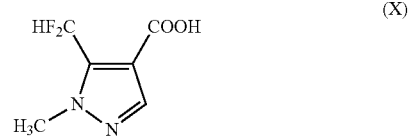

The regioisomer isomer

There remains a need for a 3-difluoromethyl-1-methyl-1H-pyrazole-4-carboxylic acid synthesis with a highly efficient Claisen condensation reaction workup, which has advantages of high yield, simple and safe operation, short workup time, and no or minimal chemical waste generation. There also remains the need for a highly effective drying method to remove residual water prior to the alkyl orthoformate coupling and a highly efficient ring closure system. The method described in this disclosure meets all these objectives and provides additional advantages.

SUMMARY

The inventors surprisingly found that distilling the enolate salt formed by the Claisen condensation, and thereby removing residual water, alkyl acetate, and alkyl alcohol before acidification can avoid all disadvantages of previously published methods and can increase the Claisen condensation by 10-15%.

The disclosure provides a process for producing a compound of Formula I

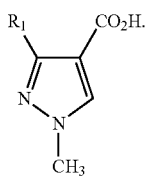

(I)

In a first embodiment the disclosure provides a method for producing a compound of Formula XVI

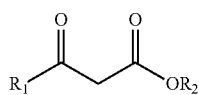

(XVI)

comprising:
(a) reacting compounds of Formula III, XIII, and XIV to produce an enolate salt of Formula XV and alkyl alcohol;

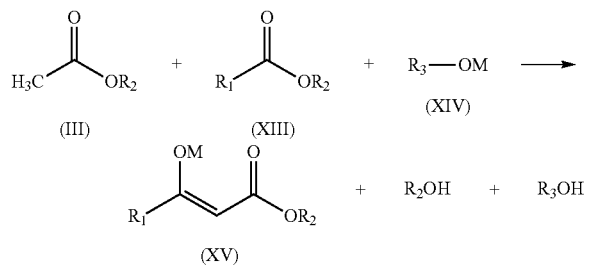

(b) distilling the enolate salt of Formula XV to remove Formula XIII and the alkyl alcohol to provide a purified enolate salt of Formula XV; and
(c) acidifying the purified enolate salt of Formula XV to provide the compound of Formula XVI

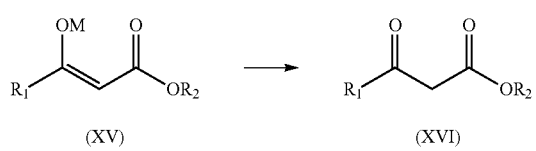

wherein:
$R_1$ is $CF_2H$, $CFH_2$, $CF_3$, $CCl_2H$, $CClH_2$, or $CCl_3$;
$R_2$ is $C_1$-$C_6$ alkyl;
$R_3$ is methyl or ethyl; and
M is sodium, potassium, or lithium.

The process may additionally comprise
(d) coupling the compound of Formula XVI with a trialkyl orthoformate of Formula XVII to provide a compound of Formula XVIII

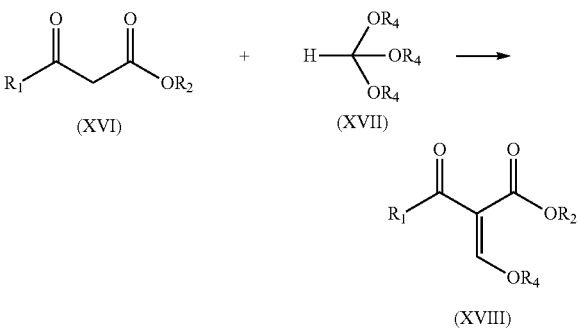

wherein $R_4$ is $C_1$-$C_6$ alkyl.

The process may additionally comprise
(e) reacting the compound of Formula XVIII with methyl hydrazine hydrate ($H_3CNHNH_2 \cdot H_2O$) to provide a compound of Formula XII

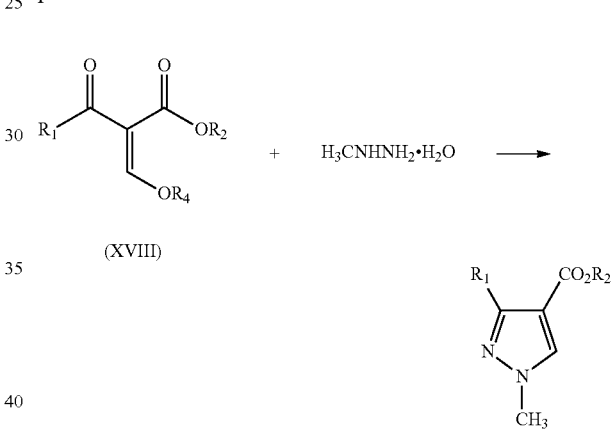

The process may additionally comprise
(f) basic hydrolysis of the compound of Formula XII followed by acidification with a strong acid

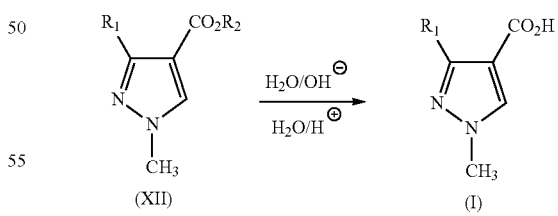

to provide a compound of Formula I.

DETAILED DESCRIPTION

The process set forth in the SUMMARY section proceeds as follows. When disappearance of the starting material, alkyl difluoroacetate, via GC analysis, indicates the Claisen condensation is complete, the reaction mixture is concentrated to remove residual alkyl acetate and alkyl alcohol. The stable enolate salt (Formula XV) precipitates as a yellowish or an off-white basic solid in the reactor.

The basic solid is cooled to 5-15° C., and acidified with 5-15% hydrochloric acid (pre-cooled to 5-10° C.) to pH=1-3. Dichloromethane or toluene is then added to extract the alkyl haloacetoacetate (Formula XVI). The two phases are separated. The aqueous phase is re-extracted by dichloromethane or toluene. The organic phases are combined and directly concentrated to remove most of the solvent and water without using any drying agent.

A highly effective drying method that scavenges residual water from the two-phase separation of Formula XVI is also provided.

Water, even if present in small quantity causes alkyl haloacetoacetate decomposition and is also highly detrimental to the subsequent coupling reaction. The presence of water decreases yield and generates by-products from the coupling reaction.

The disclosure provides a method of reacting trialkyl orthoformate of Formula VIII with water under acidic conditions, hydrolyzing the trialkyl orthoformate to alkyl formate of Formula IX and alcohol. The reaction is rapid, irreversible and quantitative.

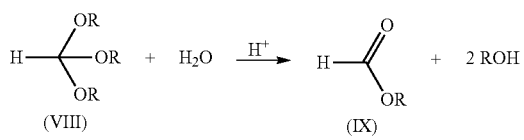

R = Alkyl

The inventors surprisingly found that applying this reaction before starting the coupling reaction of alkyl haloacetoacetate (Formula V) and trialkyl orthoformate destroys virtually all residual water carried on from the Claisen condensation reaction workup, and drops the water content of the reaction mixture from 2-3% to 100-300 ppm or even as low as 10-50 ppm or less.

Accordingly, the separated dichloromethane or toluene organic phase containing alkyl haloacetoacetate is placed in a reactor, to which the calculated amount (based upon the amount of the existing water) of trialkyl orthoformate is added, followed by adding the catalytic amount of a strong acid, such as $H_2SO_4$, HCl, or p-TSA at 20-30° C. The reaction is agitated continually for 2-3 hours. Alkyl haloacetoacetate has a higher boiling point than the alkyl formate and alkyl alcohol generated in the hydrolysis. Thus the alkyl formate and alkyl alcohol can then be easily removed by concentration of alkyl haloacetoacetate. The dry alkyl haloacetoacetate thus prepared is left in the reactor for the subsequent coupling reaction. Alternatively, the generated alkyl formate and alkyl alcohol can remain in the reaction mixture undisturbed while proceeding to the trialkyl orthoformate coupling step.

The disclosure further provides a novel ring-closure procedure that produces high purity alkyl 3-difluoromethyl-1-methyl-1H-pyrazole-4-carboxylate (Formula VII) in high yield.

The disclosure provides a ring-closure reaction, which can be performed in a two phase system and provides a higher yield and higher purity of the product of the Formula VII than previously disclosed methods. The ring closure reaction is promoted by bases such as $K_2CO_3$ or $Na_2CO_3$, bases which are much weaker than those such as KOH or NaOH used in previously reported methods.

The inventors also surprisingly found that the 2-methyl substituted positional isomer of Formula XI and defluorinated impurity (XX) dissolve in a toluene: petroleum ether/1:2-7 mixed solvent system. Both remain in the mother liquor and can be easily removed during the filtration of the product (Formula VII), eliminating the need for additional recrystallizations of the final product of Formula I.

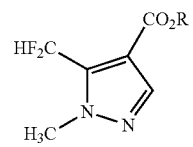

The ester positional isomer

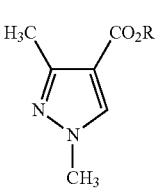

The defluorinated impurity

Additional Embodiments

In addition to the processes discussed in the SUMMARY section the disclosure provides embodiments of this process in which any of the following conditions are met. Any of the following steps or conditions may be combined so long as a reaction or reactions disclosed in the SUMMARY section proceeds.

An embodiment includes a process as set forth in the SUMMARY section, additionally comprising removing residual water from the compound of Formula XVI by hydrolysis with trialkyl orthoformate prior to coupling the compound of Formula XVI with the trialkyl orthoformate.

In an embodiment the hydrolysis with trialkyl orthoformate is catalyzed with an acid.

In an embodiment the hydrolysis with trialkyl orthoformate is catalyzed by a strong protic acid selected from a group consisting of $H_2SO_4$, $HNO_3$, HCl, HBr, HI, TFA, $H_3PO_4$, p-TSA and MSA.

In an embodiment the trialkyl orthoformate is a tri($C_1$-$C_6$) alkyl orthoformate.

In an embodiment the acidification of the enolate metal salt of Formula XV is conducted between about 0° C. and about 40° C., or preferably between about −20° C. to about 30° C., or −20° C. to −30° C.

In an embodiment the compound of Formula XVI is extracted by a water-immiscible solvent, a low water-miscible organic solvent, or a mixture of a water-immiscible solvent and a low water-miscible organic solvent.

In an embodiment the reaction compound of Formula XVIII with methyl hydrazine hydrate occurs in a two-phase solvent.

In an embodiment the reaction of a compound of Formula XVIII with methyl hydrazine hydrate occurs in a two-phase solvent, in which the two phase solvent contains an organic phase and an aqueous phase and the organic phase contains a water-immiscible organic solvent, a low water-miscible organic solvent, or a mixture of a water-immiscible organic solvent and a low water-miscible organic solvent.

In an embodiment the reaction of the compound of Formula XVIII with methyl hydrazine hydrate is conducted in the presence of $Na_2CO_3$, $K_2CO_3$, $Li_2CO_3$, $CaCO_3$, $MgCO_3$, or a combination of any of the foregoing.

In an embodiment the reaction of the compound of Formula XVIII with methyl hydrazine hydrate is conducted between about –20° C. and about 50° C.

In an embodiment the compound of Formula XII is purified by precipitation in a solvent mixture.

In an embodiment the compound of Formula XII is purified by precipitation in a solvent mixture, and the solvent mixture is selected from the group consisting of toluene/petroleum ether, toluene/hexane, toluene/pentane, toluene/heptane, toluene/cyclohexane, toluene/ethyl acetate, toluene/isopropyl acetate, toluene/butyl acetate and toluene/MTBE.

In an embodiment the compound of Formula XII is purified by precipitation in a solvent mixture and the precipitation occurs between about 0° C. and about –25° C. or –20° C. to 30° C.

In an embodiment $R_1$ is $CF_2H$ or $CF_3$, $R_2$ is ethyl, $R_3$ is ethyl, M is sodium, and $R_4$ is ethyl. In an embodiment $R_1$ is $CF_2H$.

In an embodiment, the reaction of Formula XVIII with methyl hydrazine hydrate or methyl hydrazine occurs in a two phase solution, and the organic phase comprises toluene. Further, the aqueous phase may be removed after the reaction of Formula XVIII with methyl hydrazine hydrate or methyl hydrazine, and the reaction product Formula XII and reaction by-products may be concentrated in toluene.

An embodiment includes adding a mixture of toluene and petroleum ether to a mixture of the product of Formula XII and reaction by-product concentrated in toluene and thereby precipitating the product of Formula I and removing the reaction by-products by filtration.

Terminology

Compounds are described using standard nomenclature. Unless defined otherwise, all technical and scientific terms used herein have the same meaning as is commonly understood by one of skill in the art to which this invention belongs.

The term "Formula I" encompasses all compounds that satisfy Formula I, including any enantiomers, racemates and stereoisomers, and so forth, of such compounds. "Formula I" includes all subgeneric groups of Formula I, such compounds of Formula I in which $R_1$ or $R_2$ carries a particular definition, unless clearly contraindicated by the context in which the term "Formula I" is used. Formula I includes both the generic formula in which $R_1$ is $CF_2H$, $CFH_2$, $CF_3$, $CCl_2H$, $CClH_2$, or $CCl_3$ and the preferred form in which $R_1$ is $CF_2H$.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Compounds of Formula I include all compounds of Formula I having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_5$alkyl, $C_1$-$C_4$alkyl, and $C_1$-$C_2$alkyl. Examples of alkyl include, but are not limited to, methyl, ethyl, n-propyl, isopropyl, n-butyl, 3-methylbutyl, t-butyl, n-pentyl, and sec-pentyl.

EXAMPLES

Example 1

The Preparation of Ethyl Difluoroacetoacetate

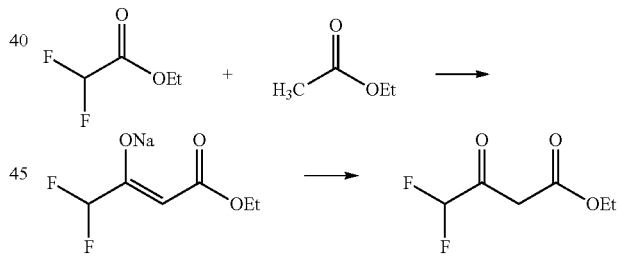

Ethyl difluoroacetate (124.1 g, 1.00 moles) is mixed with ethyl acetate (176.2 g, 2.00 moles) under nitrogen at room temperature. Sodium ethoxide (71.5 g, 1.05 moles) is added portion-wise. The addition is exothermic to bring temperature gradually to 40-55° C. The mixture is heated up to 60-65° C. and kept for 2 hours. GC test indicates a conversion >98.0%.

The transparent yellow-brownish liquid is concentrated under vacuum to remove ethanol and ethyl acetate. The pale-yellow solid precipitates in the flask, and is cooled to 5-10° C. Pre-cooled HCl aqueous solution (10%) is added dropwise until pH=1-3, followed by addition of dichloromethane (498 g) with effective agitation. The two phases are separated. The aqueous phase is removed and extracted with dichloromethane.

The product remains in dichloromethane with a yield of 95% by GC quantification with internal standard analysis. The water content in the dichloromethane is 2-3%.

Example 2

Ethyl Difluoroacetoacetate Drying Procedure Using Excess Hydrochloric Acid as a Catalyst The crude ethyl difluoroacetoacetate (~0.95 moles) in dichloromethane (~498 g) is concentrated to ⅛-⅙ of the total volume. The mixture is cooled to 20-30° C., to which the calculated amount of triethyl orthoformate (1.2 equivalents based on existing water) is added. The mixture is stirred at 20-30° C., and 2-3 hours at the same temperature. Dichloromethane, the formed ethyl formate and ethanol are distilled away. The water content is decreased to below 300 ppm.

Example 3

The Ethyl Difluoroacetoacetate Drying Procedure in Toluene

The drying procedure is the same as that given in Example 2, except toluene is used as a solvent in place of dichloromethane. The water content is decreased to below 200 ppm.

Example 4

Preparation of Ethyl Trifluoroacetoacetate

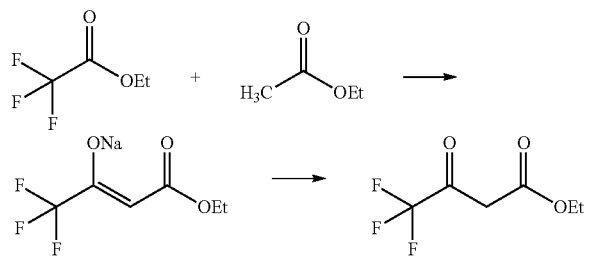

Ethyl trifluoroacetate (142.1 g, 1.00 moles) is mixed with ethyl acetate (229.1 g, 2.60 moles) under nitrogen at 5-10° C. Sodium ethoxide (71.5 g, 1.05 moles) is added portion-wise at the same temperature. The addition is exothermic, bringing the temperature gradually to 40-55° C. The mixture is heated to 60-65° C. and kept at that temperature for 3 hours. GC indicates a conversion of 98.8%.

The yellow-brownish liquid is concentrated under vacuum to remove ethanol and ethyl acetate. A pale-yellow solid precipitates in the flask and is cooled to 5-10° C. Pre-cooled HCl aqueous solution (15%) is added dropwise until pH=1-3, followed by addition of dichloromethane (450 g) with effective agitation. The two phases are separated.

The aqueous phase is removed and extracted with dichloromethane. Water content in the dichloromethane is 1-2%.

Example 5

The Ethyl Trifluoroacetoacetate Drying Procedure Using Concentrated Sulfuric Acid (98%) as a Catalyst The crude ethyl trifluoroacetoacetate (~0.98 moles) in dichloromethane (~500 g) is concentrated to ⅛-⅙ of the total volume. The mixture is cooled to 20-30° C., to which the calculated amount of triethyl orthoformate (1.2 equivalents based on existing water) and a catalytic amount of $H_2SO_4$ (10-20 ppm based on the total weight of the reaction mixture) are added. The mixture is stirred at 20-30° C. for 2-3 hours. Dichloromethane, the formed ethyl formate, and ethanol are distilled off. The obtained crude liquid is used directly in the next step. The residual water content is below 100 ppm at the end of this procedure.

Example 6

Preparation of Ethyl 2-Ethoxymethylenedifluoroacetoacetate

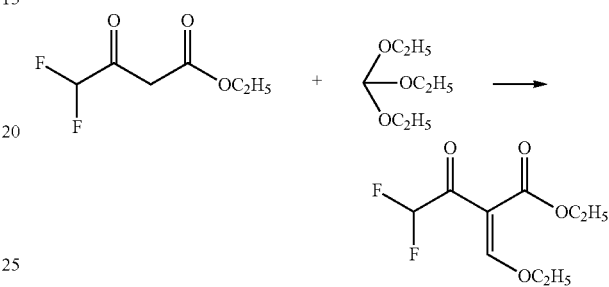

To the concentrated product of crude ethyl difluoroacetoacetate (~0.93 mole) are added triethyl orthoformate (266.8 g, 1.8 moles) and acetic anhydride (367.6 g, 3.6 moles). The mixture is heated to 90-95° C., and kept gently refluxing for 6 hours. (GC shows ethyl difluoroacetoacetate content <0.1%). The reaction mixture is cooled to 60-70° C. and then concentrated under vacuum to remove excess acetic anhydride, triethyl orthoformate, and generated ethyl acetate. A pale brown liquid (178.6 g) is obtained. The yield of two steps is 80%.

Example 7

Preparation of Ethyl 2-Ethoxymethylenetrifluoroacetoacetate

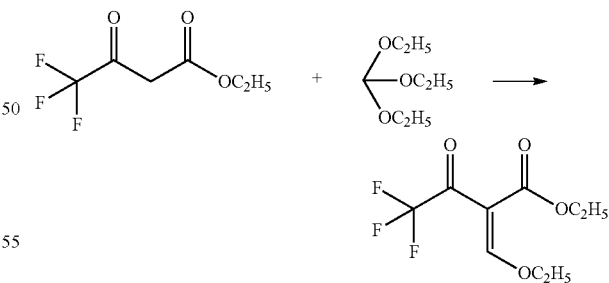

The acetic anhydride (367.6 g, 3.6 moles) is heated to 100-105° C., to which a mixture of crude ethyl trifluoroacetoacetate (~0.96 mole) and triethyl orthoformate (266.8 g, 1.8 moles) is added drop-wise. The reaction mixture is kept at 100-105° C. for 6 hours. The reaction mixture is cooled to 60-70° C. and then concentrated under vacuum to remove excess acetic anhydride, triethyl orthoformate, and generated ethyl acetate. A pale brown liquid (194.6 g) is obtained. The yield of two steps is 81%.

Example 8

Preparation of Ethyl 3-Difluoromethyl-1-Methyl-1H-Pyrazole-4-Carboxylate

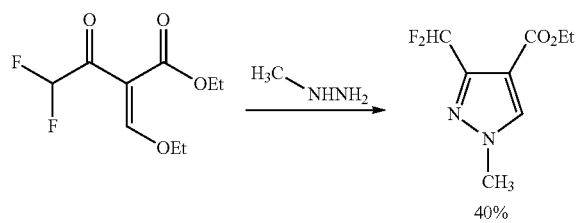

40% Methylhydrazine (565 g, 4.91 moles) in aqueous solution and K$_2$CO$_3$ (237 g, 1.72 moles) are dissolved in water (2134 g) and mixed to make a clear solution. Toluene (2292 g) is added to make a two phase system, and then cooled to −10-0° C. Crude ethyl 2-ethoxymethylenedifluoroacetoacetate (Formula VI) (~1010 g, ~4.91 moles) in toluene (1500 g) is then added dropwise with effective agitation while maintaining at the same temperature. The agitation is kept constant for 1-2 hours until GC shows the content of ethyl 2-ethoxymethylenedifluoroacetoacetate <0.2%. Two phases are separated and the organic phase is concentrated until GC shows toluene content <5%. A mixture of toluene (757 g) and petroleum ether (3028 g) (bp. 60-90° C.) is added in and then heated up to 50-60° C. to make a solution. The yellowish solid precipitated after the solution is slowly cooled down to 10-15° C. The solid is collected by filtration and dried in a vacuum oven to give a yellowish solid (828 g, Yield=82.5%). The product only contains 0.01% of the positional isomer of formula XI and 0.01% of the des-difluoro-impurity of Formula XII.

Example 9

Preparation of Ethyl 3-Trifluoromethyl-1-Methyl-1H-Pyrazole-4-Carboxylate

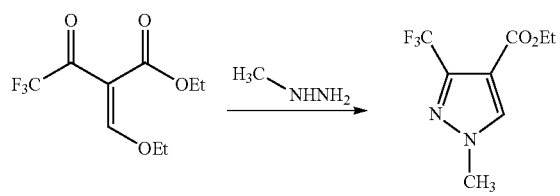

The reaction process is the same as for the preparation of ethyl 3-difluoromethyl-1-methyl-1H-pyrazole-4-carboxylate given in Example 8. The yield is 84.5%. The purity is 99.80%.

We claim:

1. A process for producing a compound of Formula XVI

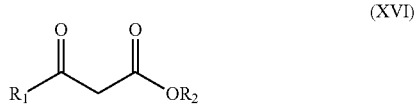

comprising:

(a) reacting compounds of Formula III, XIII, and XIV to produce an enolate salt of Formula XV and alkyl alcohol;

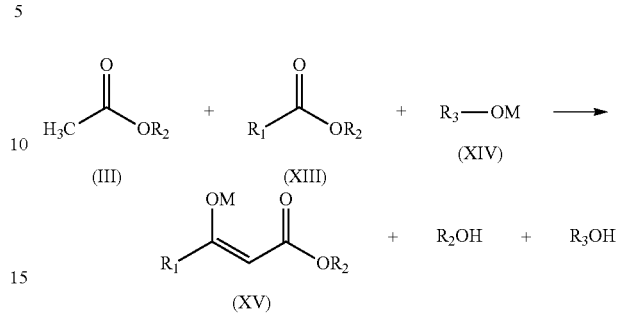

followed by (b), wherein (b) consists essentially of distilling the enolate salt of Formula XV wherein the distillation removes residual Formula XIII and the alkyl alcohol to provide a purified enolate salt of Formula XV; and then (c) acidifying the purified enolate salt of Formula XV to provide the compound of Formula XVI

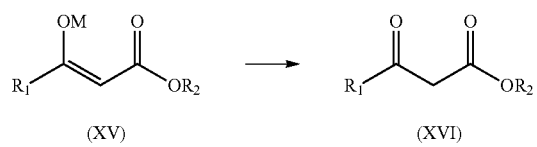

wherein:

R$_1$ is CF$_2$H, CFH$_2$, CF$_3$, CCl$_2$H, CClH$_2$, or CCl$_3$;

R$_2$ is C$_1$-C$_6$ alkyl;

R$_3$ is methyl or ethyl; and

M is sodium, potassium, or lithium.

2. The process of claim 1, further comprising:

(d) coupling the compound of Formula XVI with a trialkyl orthoformate of Formula XVII to provide a compound of Formula XVIII

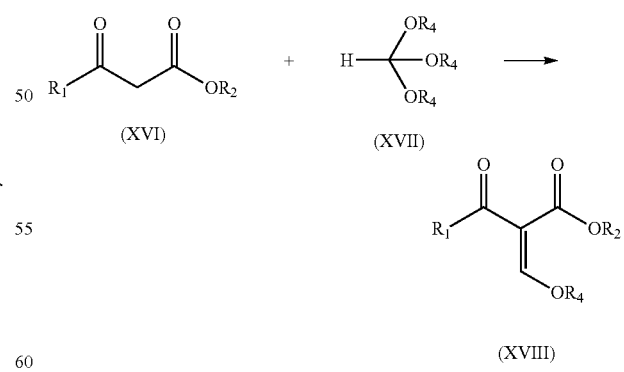

R$_4$ is C$_1$-C$_6$alkyl.

3. The process of claim 2, additionally comprising:

(e) reacting the compound of Formula XVIII with methyl hydrazine hydrate (H$_3$CNHNH$_2$.H$_2$O) or methyl hydrazine to provide a compound of Formula XII

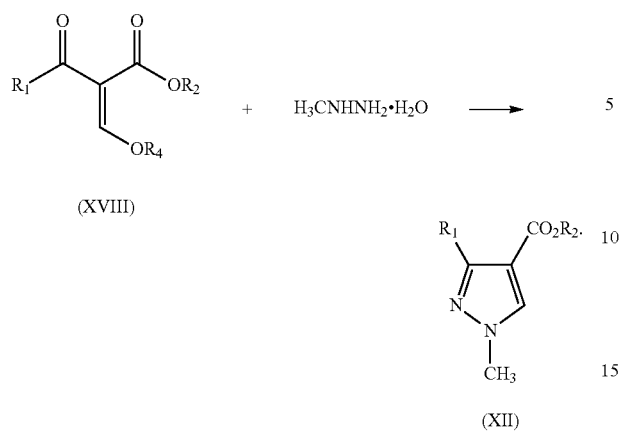

(XVIII)   +   H₃CNHNH₂·H₂O   →   (XII)

4. The process of claim 3, additionally comprising
 (f) basic hydrolysis of the compound of Formula XII followed by acidification with a strong acid

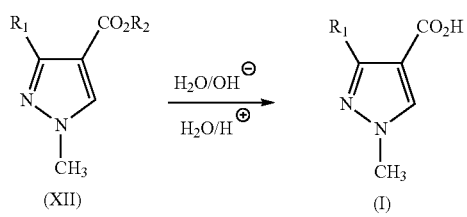

to provide a compound of Formula I.

5. The process of claim 1 additionally comprising: removing residual water from the compound of Formula XVI by hydrolysis of trialkyl orthoformate prior to coupling the compound of Formula XVI with trialkyl orthoformate.

6. The process of claim 5, wherein the hydrolysis of trialkyl orthoformate is catalyzed with an acid.

7. The process of claim 6, wherein the hydrolysis of trialkyl orthoformate is catalyzed by a strong protic acid selected from a group consisting of $H_2SO_4$, $HNO_3$, HCl, HBr, HI, TFA, $H_3PO_4$, p-TSA and MSA.

8. The process of claim 2, wherein the trialkyl orthoformate is a tri($C_1$-$C_6$)alkyl orthoformate.

9. The process of claim 1, wherein the acidification of the enolate metal salt of Formula XV is conducted between about −20° C. to about 30° C.

10. The process of claim 1, wherein the compound of Formula XVI is extracted by a water-immiscible solvent, a low water-miscible organic solvent, or a mixture of a water-immiscible solvent and a low water-miscible organic solvent.

11. The process of claim 3, wherein the reaction of the compound of Formula XVIII with methyl hydrazine hydrate occurs in a two-phase solvent.

12. The process of claim 11, wherein the two phase solvent contains an organic phase and an aqueous phase and the organic phase contains a water-immiscible organic solvent, a low water-miscible organic solvent, or a mixture of a water-immiscible organic solvent and a low water-miscible organic solvent.

13. The process of claim 3, wherein the reaction of the compound of Formula XVIII with methyl hydrazine hydrate is conducted in the presence of $Na_2CO_3$, $K_2CO_3$, $Li_2CO_3$, $CaCO_3$, $MgCO_3$, or a combination of any of the foregoing.

14. The process of claim 3, wherein the reaction of the compound of Formula XVIII with methyl hydrazine hydrate is conducted between about −20° C. and about 50° C.

15. The process of claim 3, wherein the compound of Formula XII is purified by precipitation in a solvent mixture.

16. The process of claim 15 wherein the solvent mixture is selected from the group consisting of toluene/petroleum ether, toluene/hexane, toluene/pentane, toluene/heptane, toluene/cyclohexane, toluene/ethyl acetate, toluene/isopropyl acetate, toluene/butyl acetate and toluene/MTBE.

17. The process of claim 15 or 16, wherein the precipitation occurs between about 0° C. and about 25° C.

18. The process of claim 3, wherein $R_1$ is $CF_2H$ or $CF_3$, $R_2$ is ethyl, $R_3$ is ethyl, M is sodium, and $R_4$ is ethyl.

19. The process of claim 17, wherein $R_1$ is $CF_2H$.

20. The process of claim 3, wherein the reaction of Formula XVIII with methyl hydrazine hydrate or methyl hydrazine occurs in a two phase solution, and the organic phase comprises toluene.

21. The process of claim 1, where the purified enolate salt of Formula XV is acidified with aqueous HCl to provide the compound of Formula XVI.

22. The process of claim 2, wherein step (d) is performed without distilling the compound of Formula XVI formed in step (c).

\* \* \* \* \*